(12) United States Patent
Geffen et al.

(10) Patent No.: US 6,934,019 B2
(45) Date of Patent: Aug. 23, 2005

(54) CONFOCAL WAFER-INSPECTION SYSTEM

(75) Inventors: Michael Geffen, Misgav (IL); Yaki Levi, Kiryat Ata (IL)

(73) Assignee: Camtek Ltd., Migdal Haemek (IL)

( * ) Notice: Subject to any disclaimer, the term of this patent is extended or adjusted under 35 U.S.C. 154(b) by 0 days.

(21) Appl. No.: 10/820,367

(22) Filed: Apr. 7, 2004

(65) Prior Publication Data

US 2005/0030528 A1 Feb. 10, 2005

Related U.S. Application Data

(63) Continuation of application No. PCT/IL02/00841, filed on Oct. 21, 2002.

(30) Foreign Application Priority Data

Oct. 25, 2001 (IL) ................................................ 146174

(51) Int. Cl.$^7$ ............................................... G01N 21/88
(52) U.S. Cl. ............................... 356/237.4; 356/237.5; 356/601
(58) Field of Search ........................... 356/237.2, 237.4, 356/237.5, 601, 609, 625, 630–632; 250/559.19, 559.2, 559.22

(56) References Cited

U.S. PATENT DOCUMENTS 5,963,314 A 10/1999 Worster et al.
5,991,040 A 11/1999 Doemens et al.
6,128,077 A 10/2000 Jovin et al.
6,167,148 A 12/2000 Calitz et al.

FOREIGN PATENT DOCUMENTS

| EP | 0 916 981 A1 | 5/1999 |
| FR | 2716727 | 9/1995 |
| FR | 2738343 | 3/1997 |
| WO | WO 01/51885 A1 | 7/2001 |

*Primary Examiner*—Richard A. Rosenberger
*Assistant Examiner*—Vincent P. Barth
(74) *Attorney, Agent, or Firm*—Frishauf, Holtz, Goodman & Chick, P.C.

(57) ABSTRACT

A confocal wafer inspection system including: (a) a table to carry a wafer for inspection, the table having two vertical degrees of freedom to enable XY axis movements; (b) a movement device for moving the table along the degrees of freedom; (c) a confocal height measurement system, perpendicular to the table, for measuring the range to a point on a surface of the wafer and for enabling to recognize changes in surface altitude while the wafer moves with the table; and (d) a computer operative for: (i) holding a bumps map of the wafer; (ii) controlling the movement device; (iii) moving the table so that the measuring point of the confocal height measurement system crosses each bump of the wafer; (iv) storing a height profile of each bump; (v) comparing the height profiles or checking each height profile according to predetermined criteria or both; and (vi) enabling a results output. The invention also relates to a method for confocal wafer inspection.

9 Claims, 3 Drawing Sheets

CONFOCAL WAFER-INSPECTION SYSTEM

This application is a Continuation of PCT/IL02/00841 filed Oct. 21, 2002, the contents of which are incorporated herein by reference.

FIELD OF THE INVENTION

The present invention relates to the field of checking the height of small objects, and more specifically, of three-dimensional objects by using height measurement techniques.

BACKGROUND OF THE INVENTION

A "bump" is a three-dimensional shape (half sphere or rectangular) salient, made of solder or gold located on the face of a microelectronic chip. The bump exists in some chips and substitutes as leads by means of which the component is connected to the printed circuit when the bumps are soldered to the board. The bump shape is usually a half ball alike. A chip can contain a large number of bumps, which should be of the same height in order to connect all of them to the board at the same time. Actually, there are differences between the heights of the various bumps, as a result of the production process. Only small height differences can be allowed, and these must be within the tolerance limits. Therefore the height of each bump must be checked.

Various systems for wafer-inspection are known and the main disadvantage of all those systems is a low accuracy in height measurement. Therefore, the main object of the present invention is that it uses a Confocal Height Measuring System (CHMS) to achieve accurate height measurement.

Confocal Height Measuring System (CHMS) is assembled from a confocal imaging optical setup with chromatic aberration focusing lens, a light source, an optic head that separates the light source to its basic wavelength and a spectrometer.

The confocal imaging optical setup is an optical setup for imaging a point of light source into a sharply focused second point and then reversing the image from the second point onto a tiny spatial filter. Such an optical setup is absolutely blind for all the space except for the sharply focused second point. Field extension can be obtained by stretching the chromatic aberration of the focusing lens of the setup. The new setup, with such a lens, is assembling of infinity of purely confocal systems, one for each wavelength.

Since each wavelength has a different focus length, said setup can be used as height-measuring device to measure the height of a surface point. A white light beam is separated to its basic wavelength beams by the optic head and each beam illuminates the surface. The illumination is reflected back through the confocal imaging optical setup to the spectrometer. Only one wavelength is passed the confocal imaging optical setup, according to height of the surface, which matches the focus length. The wavelength is detected by the spectrometer and translated to the height of the surface point according to a calibration table.

Confocal imaging optical setup and confocal height measuring system are described in patent application, with a French title: "Dispositif de microstratigraphie optique"—national registration number: FR9510401 and publication number: 2 738 343 and patent application, with a French title: "Dispositif de tomographie optique en champ coloré"—national registration number: FR9402489 and publication number: 2 716 727.

Since the low accuracy—in height measurement—is the main disadvantage of the known systems, there is a recognized need for, and it would be highly advantageous to have, a system and a method for wafer-inspection that uses confocal height measuring system for checking the accurate height of bumps for comparing bumps on a wafer.

SUMMARY OF THE INVENTION

The present invention is a confocal wafer-inspection system.

According to the teachings of the present invention there is provided a confocal height measuring system wafer-inspection system including:

(a) a table, to put on a wafer for inspection, this table has two vertical degrees of freedom, enables XY axis movements;

(b) a movement-means for move the table along the vertical degrees of freedom;

(c) a confocal height measuring system, perpendicular to the table, for measuring the range to a point on a surface of the inspected wafer, enables to recognize changes in surface altitude while the wafer moves with the table; and (d) a computer operative for:
  (i) holding a bumps map of the inspected wafer;
  (ii) controlling the movement means;
  (iii) moving the table so that the measuring point of the confocal height measurement system crosses each bump of the wafer;
  (iv) storing the height profile of each bump;
  (v) comparing the height profiles and checking each height profile according to predetermined criteria; and
  (vi) display results.

By one preferred embodiment the wafer-inspection system, further includes:

(e) a microscope, integrated with the confocal height measurement system, to observe the inspected wafer surface; and (f) a first camera for photographs the observed surface.

By second preferred embodiment the wafer-inspection system, further includes a vertical movement means for elevate and lower the microscope and the confocal height measurement system.

By another preferred embodiment the wafer-inspection system, further includes a second camera for scanning the inspected wafer, than the image or images of the scanning are used by the computer to recognize bumps, the computer stores location of the recognized bumps and built a bumps map to be held by the computer.

By another preferred embodiment the second camera of the wafer-inspection system is a digital camera.

By another preferred embodiment the second camera of the wafer-inspection system is a line-scan camera.

By yet another preferred embodiment of the wafer-inspection system, the vertical movement means enables elevate and lower the second camera.

According to another aspect of the present invention, it provides a method for accurate inspection of a wafer, includes the following steps:

(a) obtaining a digital image of a wafer, using one of the following techniques:
  (i) photographing the whole wafer; or
  (ii) scanning sectors or lines of the wafer and composing a wafer image;

(b) mapping location of bumps on the wafer, by recognizing bumps in the wafer image according to predetermined criteria;

(c) planning a bumps-track line, wherein the bumps-track line crosses each bump on the wafer, at least one cross each bump;

(d) using a confocal height measurement system, located perpendicular to the wafer, to measure height changes along the bumps-track line;

(e) obtaining height profile of each bump, from the height changes along the bumps-track line; and (f) comparing and checking bumps height profile.

BRIEF DESCRIPTION OF THE FIGURES

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the figures.

DESCRIPTION OF THE PREFERED EMBODIMENTS

Figure 1:
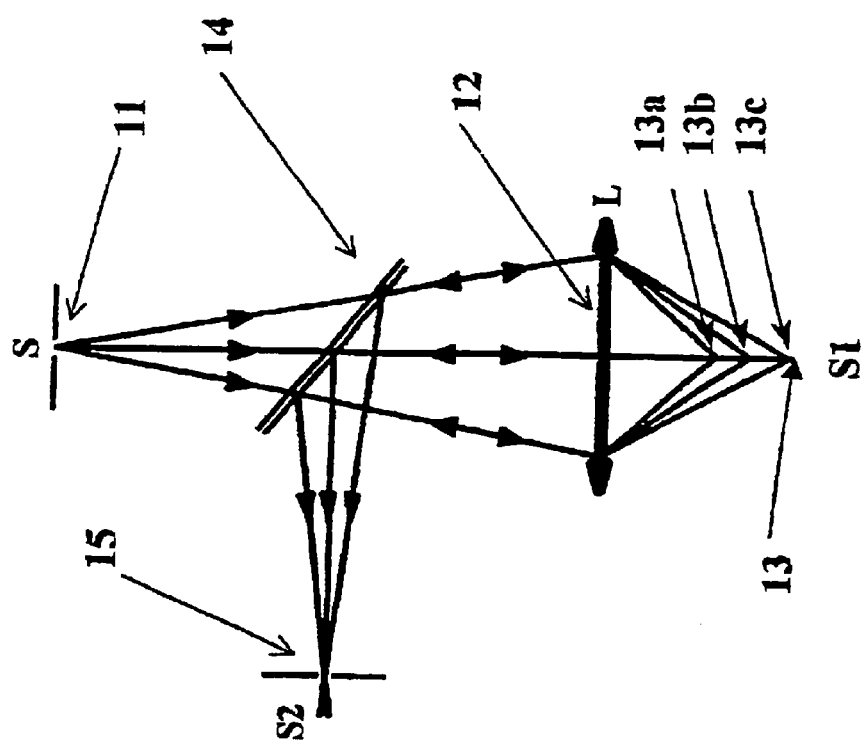
FIG. 1 illustrates the confocal optic setup.

The present invention is a confocal wafer-inspection system.

The system has a table with two vertical degrees of freedom enables a movement means to move the table in XY axis. A wafer is laying on the table and a confocal height measurement system, a microscope, a first camera and a second camera are installed perpendicular to the table, held by a horizontal movement means. A computer controls the vertical movement means and the horizontal movement means. The microscope and the confocal height measurement system are aimed to the same point.

An inspected wafer lies down on the table. The computer controls the movement of the table by the movement means, enables each point of the wafer surface being under the aim point. The microscope observes the wafer's surface and the first camera photograph the view and the image is transferred to the computer, which display the image on the screen. The image is used by an operator of the system to overview the surface and enables to determine the criteria for recognizing bumps.

The second camera scans the wafer and recognizes the location of all bumps on the wafer surface. The computer receives the scanned image, builds a map of bumps location and designed a bumps-track along the wafer surface, which crosses at least one time each of the bumps. The computer leads the table, by means of the vertical movement means, so that the bumps-track passes down the aim line along the whole bumps-track. The confocal height measurement system continually measures the wafer surface height and transfers information to the computer. When the aim line crosses a bump, the computer stores the height profile of the bump. The computer compares between bumps height or checks bumps profiles according to predetermined criteria or both and enables to have the results by any output device.

The principles and operation of the confocal wafer-inspection system according to the present invention may be better understood with reference to the drawing and the accompanying description.

As used herein in the specification and in the claims section that follows, the term "confocal height measurement system" and the like refer to the system that uses confocal technique to measure height changes on a surface by measuring distance from a constant point. The confocal height measuring system was described in details in the background section and in FIG. 1.

Referring now to the drawing, FIG. 1 illustrates the confocal optic setup. A confocal imaging optical setup is an optical setup for imaging a point of light source "S" 11 through a lens 12 into a sharply focused second point "S1" 13 and then reversing the image from the second point 13 onto a splitter 14 that reflects the image onto a tiny spatial filter "S2" 15. Such an optical setup is absolutely blind for all the space except for the sharply focused second point 13. Field extension can be obtained by stretching the chromatic aberration of the focusing lens 12 having a setup with an infinity of purely confocal systems, one for each wavelength with a different sharply focused point 13a, 13b, 13c and so on.

The field extended setup can be use as a height-measuring device to measure the height of a surface point. A white light beam is separated to its basic wavelength beams and illuminates, from light source 11, the surface through the chromatic stretched lens 12. Each color has a different focusing point, 13a, 13b or 13c. The illumination is reflected back through the splitter 14 onto the tiny spatial filter 15. Each color has a different sharply focused point; the first color has a first sharply focused point 13a, the second color has second sharply focused point 13b and the third color has a third sharply focused point 13c. Only one color arrives to the filter 15, according to height of the surface, which matches the focus length. If the surface height matches the first sharply focused point 13a, then the first color is detected, if the surface height matches the second sharply focused point 13b the second color is detected and so on. The color is detected by a spectrometer and translated to the height of the surface point according to a calibration table.

Figure 2:
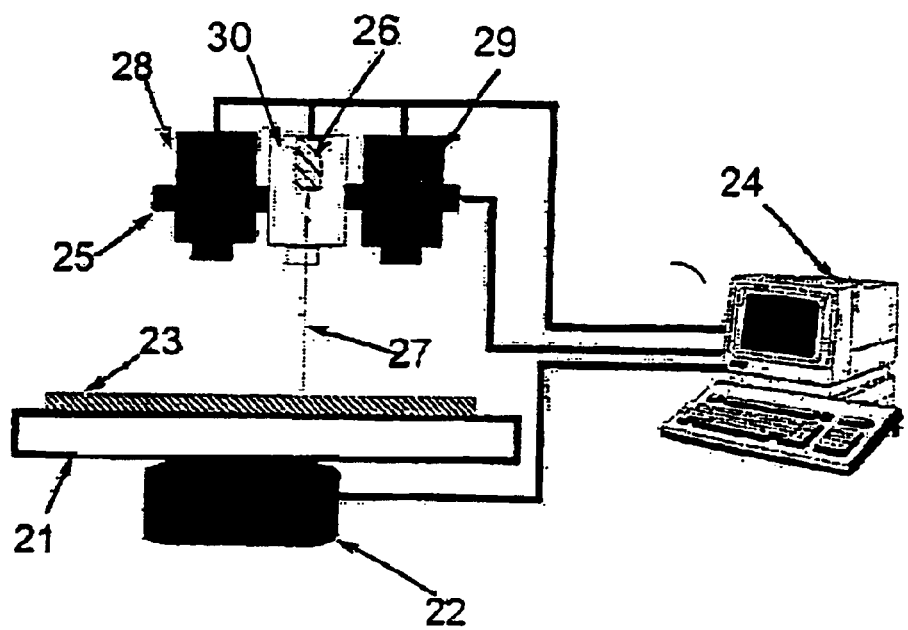
FIG. 2 illustrates an embodiment of the confocal wafer-inspection system.

FIG. 2 illustrates an embodiment of the confocal wafer-inspection system. A table 21 with two vertical degrees of freedom enables a movement means 22 to move the table 21 in XY axis. A wafer 23 is lay on the table 21 and a confocal height measurement system 26, a microscope 30, a first camera 28 and a second camera 29 are installed perpendicular to the table 21, held by a horizontal movement means 25. A computer 24 controls the vertical movement means 22 and the horizontal movement means 25. The microscope 30 and the confocal height measurement system 26 are aimed 27 to the same point.

An inspected wafer 23 lies down on the table 21. The computer 24 controls the movement of the table 21 by the movement means 22, enables each point of the wafer 23 surface being under the aim point 27. The microscope 30 observes the surface of the wafer 23 and the first camera 28 photograph the view and transfer the image to the computer 24, which display the image on the screen. The image is used by an operator of the system to overview the surface and enables to determine the criteria for recognizing bumps.

The second camera 29 scans the wafer and recognizes the location of all bumps (not shown) on the wafer surface. The computer 24 receives the scanned image, builds a map of bumps location and designed a bumps-track along the wafer surface, which crosses at least one time each of the bumps. The computer 24 leads the table 21, by means of the vertical movement means 22, so that the bumps-track passes down the aim line 27 along the whole bumps-track. The confocal height measurement system 26 continually measures the wafer 23 surface height and transfers information to the computer 24. When the aim line 27 crosses a bump (not shown), the computer 24 stores the height profile of the bump. The computer 24 compares between bumps height or checks bumps profiles according to predetermined criteria or both and enables to have the results by any output device.

Figure 3:
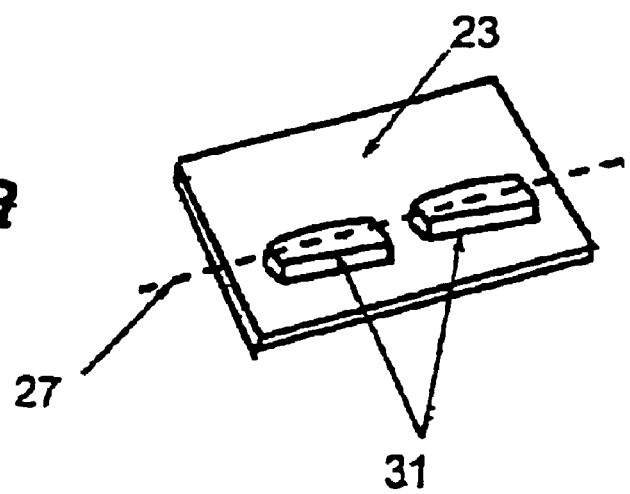
FIGS. 3a and 3b illustrate the way of obtaining profiles of bumps.
Figure 3:
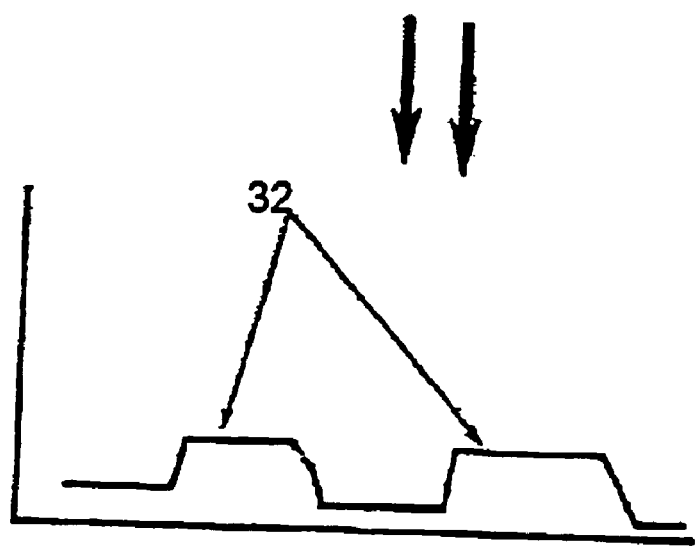

FIG. 3 illustrates the way of obtaining profiles of bumps. FIG. 3a shows a part of wafer surface 23 with bumps 31 on it. The wafer surface 23 moves according to the computer 24 controls along the bumps-track so that aim points 27 crosses the bumps 31. The confocal height measurement system 26 continually measures the bumps 31 height and transfers information to the computer 24. FIG. 3b is a graphic illustration of the confocal height measurement system 26 measurements, which contains bumps height profiles 32, these profiles will be compared by the computer 24 or checked according to predetermined criteria.

Although the invention has been described in conjunction with specific embodiments thereof, it is evident that many alternatives, modifications and variations will be apparent to those skilled in the art, accordingly, it is intended to embrace all such alternatives, modifications and variations that fall within the spirit and broad scope of the appended claims.

What is claimed is:

1. A confocal chromatic wafer-inspection system comprising:
   a table for supporting a wafer for inspection, the table being movable along an x-axis and along a y-axis in an XY plane;
   movement means for moving the table in the XY plane;
   a confocal chromatic height measurement system, perpendicular to the table, for measuring a range to a point on a surface of the wafer so as to enable recognition of changes in surface height of the wafer while the wafer moves with the table; and
   a computer operable for:
      (i) storing a bumps map of the wafer;
      (ii) controlling the movement means to move the table such that a measuring point of the confocal chromatic height measurement system crosses each bump of the wafer;
      (iii) storing a height profile of each bump;
      (iv) at least one of: comparing the height profile of each bump to height profiles of other bumps on the wafer, and checking the height profile of each bump according to predetermined criteria; and
      (v) outputting comparison results.

2. The confocal chromatic wafer-inspection system of claim 1, further comprising:
   a microscope integrated with the confocal chromatic height measurement system, for observing the surface of the wafer; and
   a first camera for photographing the observed surface of the wafer.

3. The confocal chromatic wafer-inspection system of claim 2, further comprising vertical movement means for elevating and lowering the microscope and the confocal chromatic height measurement system.

4. The confocal chromatic wafer-inspection system of claim 1, further comprising a second camera for scanning the wafer;
   wherein the computer recognizes bumps on the wafer based on at least one image captured by the second camera, and the computer creates the bumps map based on locations of the recognized bumps.

5. The confocal chromatic wafer-inspection system of claim 4, wherein the second camera comprises a digital camera.

6. The confocal chromatic wafer-inspection system of claim 4, wherein the second camera comprises one of a line-scan camera and an array camera.

7. The confocal chromatic wafer-inspection system of claim 4, wherein the second camera is elevated and lowered by the vertical movement means.

8. The confocal chromatic wafer-inspection system of claim 1, wherein the system is adapted to measure: probe marks depth and profile, ink dot height and profile, height and profile of conductors of the surface of the wafer, and wafer thickness at different stages of production of the wafer.

9. A method for confocal chromatic wafer-inspection comprising:
   obtaining a digital image of a wafer by one of (i) photographing all of the wafer, and (ii) scanning one of sectors of the wafer and lines of the wafer to compose the digital image of the wafer;
   mapping locations of bumps on the wafer by recognizing the bumps in the digital image of the wafer, based on predetermined criteria;
   planning a bumps-track that crosses each of the bumps on the wafer at least once;
   using a confocal chromatic height measurement system, positioned perpendicularly with respect to the wafer, to measure changes in height along the bumps-track;
   obtaining a height profile of each of the bumps based on the measured changes in height; and
   analyzing the height profile of each of the bumps by at least one of: comparing the height profile of each bump to height profiles of other bumps on the wafer, and checking the height profile of each bump according to predetermined criteria.

* * * * *

(12) INTER PARTES REEXAMINATION CERTIFICATE (0385th)
United States Patent
Geffen et al.

(10) Number: US 6,934,019 C1
(45) Certificate Issued: Jun. 5, 2012

(54) CONFOCAL WAFER-INSPECTION SYSTEM

(75) Inventors: Michael Geffen, Misgav (IL); Yaki Levi, Kiryat Ata (IL)

(73) Assignee: Camtek Ltd., Migdal Haemek (IL)

Reexamination Request:
No. 95/001,394, Oct. 25, 2010

Reexamination Certificate for:
Patent No.: 6,934,019
Issued: Aug. 23, 2005
Appl. No.: 10/820,367
Filed: Apr. 7, 2004

Related U.S. Application Data

(63) Continuation of application No. PCT/IL02/00841, filed on Oct. 21, 2002.

(30) Foreign Application Priority Data

Oct. 25, 2001 (IL) .................................................. 146174

(51) Int. Cl.
*G01B 11/02* (2006.01)
*G01B 11/24* (2006.01)
*G01B 11/06* (2006.01)
*G01N 21/00* (2006.01)
*G01N 21/95* (2006.01)
*G01N 21/88* (2006.01)

(52) U.S. Cl. .................... 356/237.4; 356/237.5; 356/601
(58) Field of Classification Search ................. 356/237.1
See application file for complete search history.

(56) References Cited

To view the complete listing of prior art documents cited during the proceeding for Reexamination Control Number 95/001,394, please refer to the USPTO's public Patent Application Information Retrieval (PAIR) system under the Display References tab.

*Primary Examiner* — Deandra Hughes

(57) ABSTRACT

A confocal wafer inspection system including: (a) a table to carry a wafer for inspection, the table having two vertical degrees of freedom to enable XY axis movements; (b) a movement device for moving the table along the degrees of freedom; (c) a confocal height measurement system, perpendicular to the table, for measuring the range to a point on a surface of the wafer and for enabling to recognize changes in surface altitude while the wafer moves with the table; and (d) a computer operative for: (i) holding a bumps map of the wafer; (ii) controlling the movement device; (iii) moving the table so that the measuring point of the confocal height measurement system crosses each bump of the wafer; (iv) storing a height profile of each bump; (v) comparing the height profiles or checking each height profile according to predetermined criteria or both; and (vi) enabling a results output. The invention also relates to a method for confocal wafer inspection.

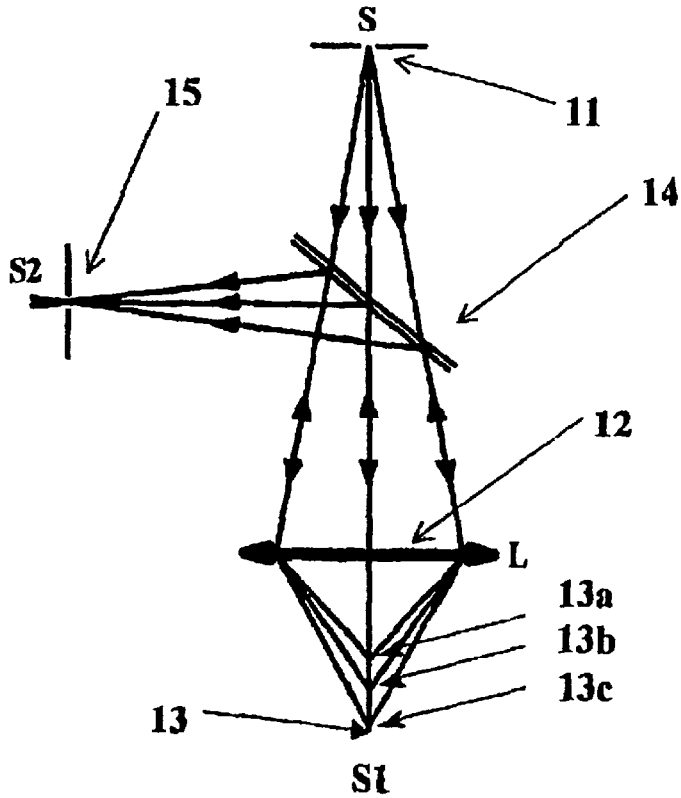

INTER PARTES REEXAMINATION CERTIFICATE ISSUED UNDER 35 U.S.C. 316

NO AMENDMENTS HAVE BEEN MADE TO THE PATENT

AS A RESULT OF REEXAMINATION, IT HAS BEEN DETERMINED THAT:

The patentability of claims 1 and 9 is confirmed.

Claims 2-8 were not reexamined.

\* \* \* \* \*